United States Patent
Lange, IV

(10) Patent No.: US 10,653,549 B2
(45) Date of Patent: May 19, 2020

(54) TOPICAL MEDICATION METHOD FOR ERECTILE DYSFUNCTION

(71) Applicant: Carl W. Lange, IV, Cuba, MO (US)

(72) Inventor: Carl W. Lange, IV, Cuba, MO (US)

(*) Notice: Subject to any disclaimer, the term of this patent is extended or adjusted under 35 U.S.C. 154(b) by 318 days.

(21) Appl. No.: 15/652,258

(22) Filed: Jul. 18, 2017

(65) Prior Publication Data

US 2019/0021897 A1    Jan. 24, 2019

(51) Int. Cl.
| | |
|---|---|
| *A61F 5/41* | (2006.01) |
| *A61K 9/00* | (2006.01) |
| *A61F 6/04* | (2006.01) |
| *A61K 9/70* | (2006.01) |

(52) U.S. Cl.
CPC .............. *A61F 5/41* (2013.01); *A61K 9/0014* (2013.01); *A61K 9/0034* (2013.01); *A61K 9/7007* (2013.01); *A61K 9/7092* (2013.01); *A61F 6/04* (2013.01); *A61F 2005/414* (2013.01); *A61F 2006/043* (2013.01)

(58) Field of Classification Search
CPC ...... A61F 5/41; A61F 6/00; A61F 6/02; A61F 6/04; A61F 6/18; A61F 6/144; A61F 6/148; A61F 6/142; A61B 5/06; A61K 9/00
See application file for complete search history.

(56) References Cited

U.S. PATENT DOCUMENTS

| | | | | |
|---|---|---|---|---|
| 6,207,713 | B1* | 3/2001 | Fossel | A61K 8/14 424/401 |
| 2007/0175484 | A1* | 8/2007 | Staab | A61F 6/04 128/844 |

FOREIGN PATENT DOCUMENTS

WO    WO-2006084305 A1 *    8/2006    ............... A61F 6/04

* cited by examiner

*Primary Examiner* — Ophelia A Hawthorne
(74) *Attorney, Agent, or Firm* — William S. Parks

(57) ABSTRACT

A novel method of applying topical erectile dysfunction medicaments for controlled dispensing thereof through a condom or like prophylactic article is provided. Additionally, encompassed within this invention is the combination of an initial ingestion of a small dose of orally taken ED medicament for initial generation of nitric oxide followed by such a topical application. With such a method, the initial oral application metabolizes and runs its course while the topical application provides the needed dose of ED medicament. Once a sexual event is completed, the wearer may then remove the topical application article removing the topical delivery thereof in order to return to a flaccid state quickly and easily. Such an article and method thus reduces the propensity for potentially damaging excessive erection states and provides a more reliable dosing regimen for more effective and safe implementation of such an ED medicament program.

2 Claims, 3 Drawing Sheets

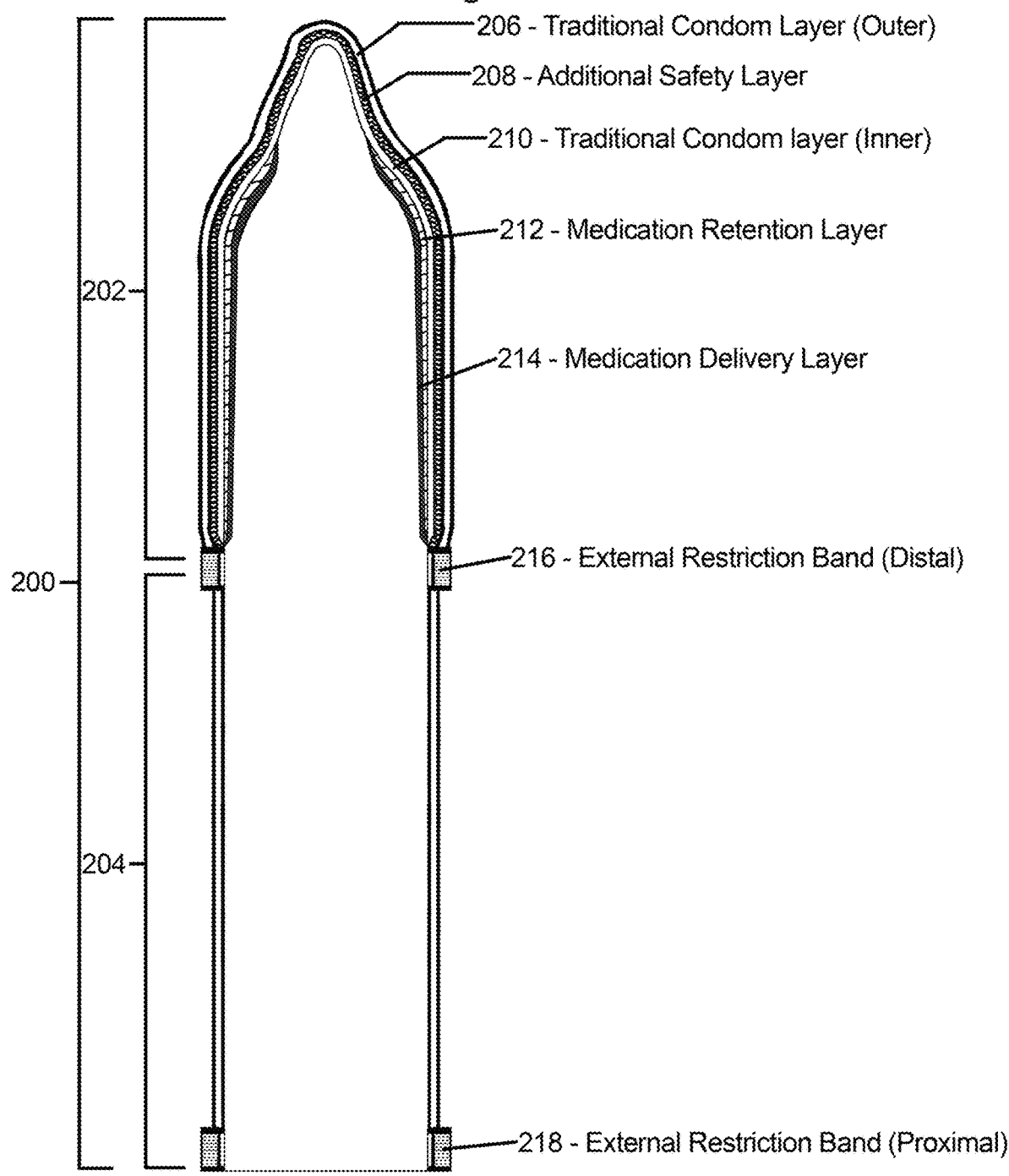

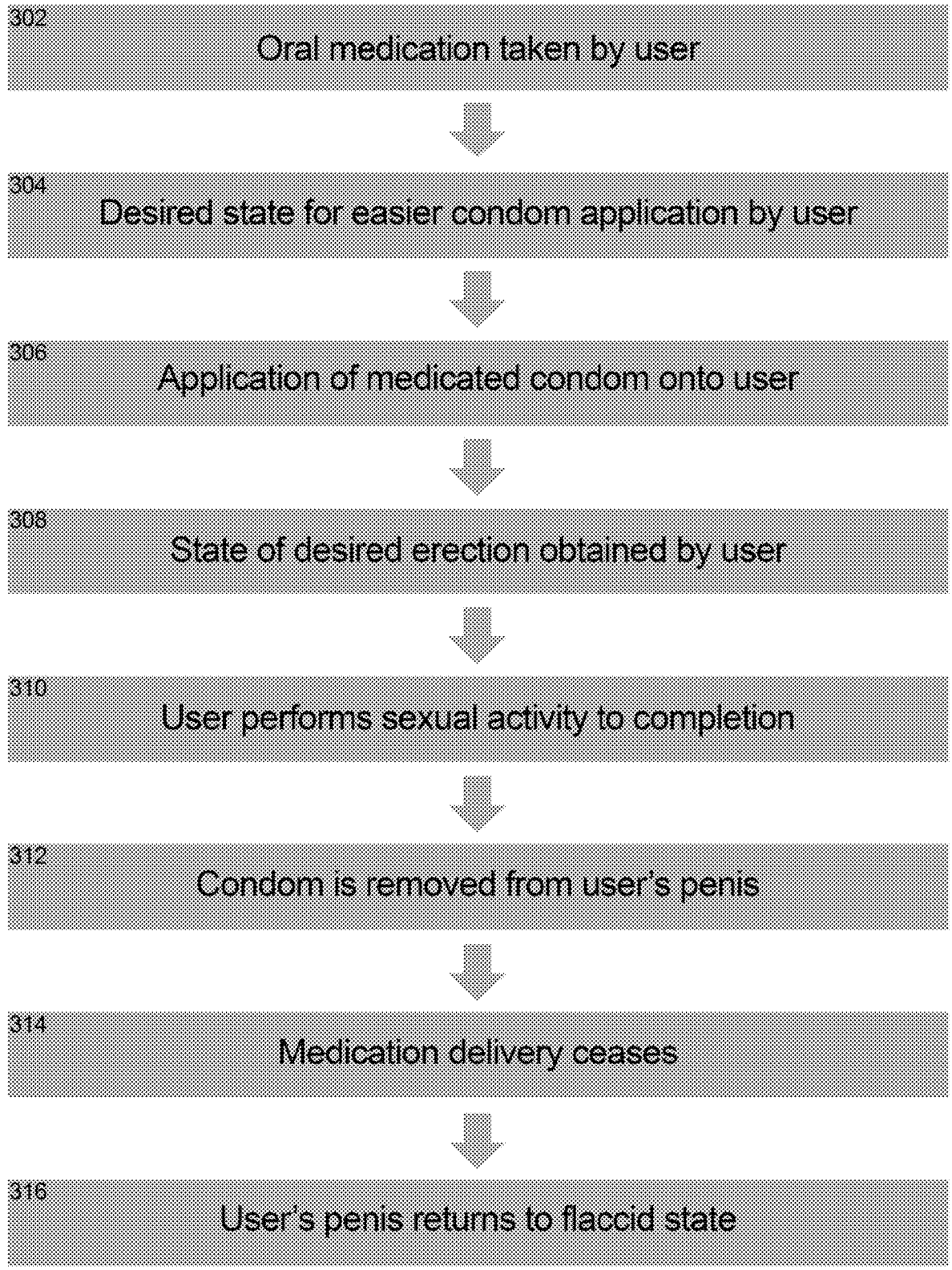

TOPICAL MEDICATION METHOD FOR ERECTILE DYSFUNCTION

FIELD OF THE INVENTION

This invention pertains to a novel method of applying topical erectile dysfunction medicaments for controlled dispensing thereof through a condom or like prophylactic article. Additionally, encompassed within this invention is the combination of an initial ingestion of a small dose of orally taken ED medicament for initial generation of nitric oxide followed by such a topical application or other such medicament that may be used for ED. With such a method, the initial oral application metabolizes and runs its course while the topical application provides the needed dose of ED medicament to provide a therapeutic effect. Once a sexual event is completed, the wearer may then remove the topical application article removing the topical delivery thereof in order to return to a flaccid state quickly and easily. Such an article and method thus reduces the propensity for potentially damaging excessive erection states and provides a more reliable dosing regimen for more effective and safe implementation of such an ED medicament program.

Background of the Prior Art|

Erectile dysfunction, as it is commonly referred to, has gained widespread understanding and acceptance within the last decade or two. The lack of either generating or keeping an erection has created problems in certain portions of the male population as sexual activity generally requires the ability to provide effective penetration; without such an erect member, the male lacks such capabilities leaving much in the way of sexual and other possible physical and mental frustrations. Although such problems have existed for eons, recent advancements have attempted to overcome these deficiencies. Actual implants, with, for instance, external electrical stimulation, have been utilized in the past, though these have never proven to be of great effectiveness, let alone, desirable to any real extent. Chemical remedies have thus been investigated with a number showing highly effective results. Such developments, including phosphodiesterase type 5 (PDE-5) inhibitors like sildenafil citrate (VIAGRA), tadalafil (CIALIS), and the like, function through oral delivery and subsequent in vivo generation of nitric oxide at or near the penis thereby causing blood to enter the sinuses therein to create the necessary erection. The problem, however, with such oral delivery methods is that the dosage provided is generally uniform and not exact or tailored for individuals. As such, and as prominently noted in advertisements therefor, the chances that an erection lasting multiple hours, and thus potentially harming the subject user, is of great concern. The ability to better deliver such nitric oxide generating compounds so the user may have greater control of his erection during sexual activity (or more precisely, subsequent thereto) would be of great interest for a safer, if not more pleasurable, experience. To date, however, although some topical delivery methods may have been disclosed, the lack of controlled procedures to enable the user to exercise desired control and reliable means to extinguish an erection post-coitus has yet to be provided within the industry. The present invention, to the contrary, allows for such an improvement with desirable effects and results.

Advantages and Brief Description of the Invention

The present invention provides a distinct advantage over previous designs by providing the user with a safe and effective means of providing a topicalized medication through a condom article at a potentially lower dose with the added ability to allow for return to flaccidity upon removal of such a topical delivery article. Another advantage is the ability to provide safe and direct topical delivery to regions of a user's penis without an appreciable propensity to contact the user's sexual partner. Yet another advantage is the ability to provide such a topical delivery article within a method that delivers a small yet effective oral dosage for initial erection generation with application of such an article thereafter for both safe sexual contact as well as birth control purposes, thus allowing for continued low, but effective, dosage of ED medicaments with the ability to remove such an article for quick return to flaccid state on demand. This is especially true for those users who may currently be on an erectile dysfunction medication.

Accordingly, this invention encompasses a male condom sheath having a closed distal region defined as covering a user's glans penis when situated over and around such a user's penis, and an open proximal region defined as the remainder of said condom having a top edge abutting said bottom edge of said distal region and a bottom edge at the opening of said condom, said condom comprising at least three layers of flexible material within the sheath thereof, wherein one of said at least three layers is an outer layer for contact with a sexual partner when in use, wherein one of said at least three layers is a material for retention of erectile dysfunction medicament therein for migration therefrom when exposed to heat and friction during a sexual activity, and wherein one of said at least three layers is an inner layer material for erectile dysfunction medicament delivery to the surface of said user's skin within said distal region thereof said condom; wherein said condom further includes a flexible, pressure ring at the bottom edge of said distal region and a second flexible, pressure ring at the bottom edge of said proximal region. The invention further encompasses a method of utilizing such a male condom as described above, the method comprised providing said male condom to a user, providing an oral erectile dysfunction medicament to the same user, wherein said oral medicament includes a dosage level of at most 50% of the typical oral dose, a level that allows for the generation of an initial erection for said user to the extent that said male condom may then be placed over and around said initial erection, the undertaking of sexual activity by said male user with said male condom remaining in place until ejaculation has been attained or such sexual activity ceases, and subsequent removal thereof of said male condom from said user's erection, thereby resulting in the lack of further topical medicament in contact with said user's penis thus allowing for return of said penis to flaccid state.

Such results and method are accomplished by containing the erectile dysfunction medicament in a male condom which would allow the user to receive a definite and consistent dose thereof as compared with previous oral (and some topical) delivery methods which did not exhibit such dosing operations. The condom design is one which can allow for safety features that further protect the user and their sexual partner(s) from potential complications with such medications. In the preferred embodiment, this can be used as a standalone element or in conjunction with other forms of medications, particularly in the case of erectile dysfunction (ED).

A common problem in previous methods of topical medication delivery to the penis is that a definite and consistent dose could not be delivered. Previous forms, whether in a condom or not, could potentially be difficult to give an appropriate amount of the medication. By having the means to pre-package the allotted amount of medication in a contained area that would not leak prior to use, this issue could potentially be avoided. One way to contain the allotted amount of medication in a safe manner is to place it in a condom, certainly, but prior articles of this type were not suitably designed for complete efficacy and/or safety (particularly for a sexual partner). In previous topical application condom procedures, risk of medicament leaking was significant, for example. Some ED medications are known to act as phosphodiesterase-5 (PDE-5) inhibitors that could have a significant impact on individuals utilizing, for instance, nitroglycerin or other like nitrate-based prescriptions. Such PDE-5 inhibitors interact deleteriously with such nitrates and topical contact with a sexual partner undertaking a regimen with such drugs could prove harmful, if not fatal. Thus, potential problems existed due to the potential for leaking from the subject condom externally to the sexual partner. Safety measures must therefore be in place to allow for the safest delivery of topical ED medicaments delivered in the form of a male condom which was lacking in the past.

The preferred embodiment of the device could be divided into two main sections. In the first section, the condom could consist of three layers: a traditional condom layer (rubber, latex, etc.), a medication retention layer, and a medication delivery layer. This section would be for the area of the glans penis where the medication is to be primarily absorbed. The second section could be a single layer consisting of the traditional condom layer. This layer would extend the length of the condom which would optimally extend to the base of the penis shaft. In both plies, the traditional condom layer would have measures to prevent breakage in normal use.

Other iterations could include additional layers. For example, certain safeguard layers to help promote additional prevention of leaking materials could be used especially between the traditional condom layer and the medication retention layer. Such safeguards could include products that absorb the medicament if it were to break through the medication retention layer externally. Optimally, this would have a separation between the aforementioned layers so as not to neutralize one another.

Although medication would only be in the first section, it is preferred to have the safety measures throughout the length of the condom for multiple reasons. The first is that although the goal is to have an optimally fitting condom that would not have any leak between the first and second sections of the condom, the potential does exist in some cases. By allowing safety measures throughout the length of the condom, should any of the medication leak to the second section, it will remain contained in the same manner as the first section. This allows for a safer delivery of the medication should there be any break in the traditional condom layer(s).

There are many biocompatible materials that can be potentially used to act as the medication retention layer. The medication retention layer, since in its preferred embodiment would be directly against the medication, would not neutralize the medication but would be designed to prevent the condom from ripping, leaking, tearing, or otherwise coming out. However, a neutralizing agent could be added if the medication does not actually come in contact with the medication retention layer unless a leak were to occur. Such an instance would be in the example above where it would be between the traditional condom layer and the medication retention layer. In this case, should the condom layer rip, the medication would now be exposed to the neutralizing agent. This layer would then safely neutralize the medication so that it would not leak out further, especially in a way which could be harmful to the patient.

The medication retention layer, in its preferred embodiment, is to be designed in such a way as that it would not rip. This is especially true in the normal use of a condom. The material would need to be of one that can stretch beyond its original dimensions. Potentially, a layer could be designed so that it withstands significant stress such as shearing. For that purpose, materials such as natural or synthetic rubber may be implemented. Additionally, though, it is desirable to have the condom article exhibit stretch under stress and return to substantially the original size after release. For such high levels of hysteresis, the condom may include a highly viscous material, and/or a combination of materials, including, without limitation, dextrose, maltose, maltotriose, and higher saccharides.

Other materials can be used to allow for stretching while also being able to absorb materials. As with most of the following iterations mentioned, this would be used in conjunction with other materials to form a layer, including, without limitation, slow recovery elastomer materials. Such elastomeric polymers may function in such a capacity at standard body temperature, as well. Broadly speaking, such materials may be block copolymers of a variety of different flexible base monomers. Thermoplastic polymers, bacteriostats, viscosity modifiers, processing aids, slip agents, or anti-block agents could also be employed, especially if a slow recover elastomer is to be used. Such a material would further allow the medication retention layer, like the rest of the condom, to stretch and help contain the medication at the same time.

Further materials that may be employed within such layers include, without limitation, absorbent bio-compatible materials, such as, again, without limitation, comminuted wood pulp; creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. A number of absorbent materials can be used such as hydrolyzed acrylonitrile grafted starch, acrylic acid grafted starch, polyacrylates, copolymers of isobutylene, and maleic anhydride. Synthetic fibers such as polyester, polyolefin, rayon, or the like, or natural fibers such as cotton, may be used. These are typically bound together by a thermal binding procedure or by a polymeric binder such as polyacrylate. Hydrogel polymers include polyacrylamides, polyvinyl alcohol, ethylene maleic anhydride copolymers, polyvinyl ethers, hydroxypropyl cellulose, carboxymethyl cellulose, polyvinyl morpholinone, polymers and copolymers of vinyl sulfonic acid, polyacrylates, polyacrylamides, polyvinyl pyridine exist. Hydrophilic fibrous materials include cellulose fibers, rayon, and polyester fibers. Other examples of suitable hydrophilic fibrous materials include hydrophilized hydrophobic fibers, such as surfactant-treated or silica-treated thermoplastic fibers. For reasons of availability and cost, cellulose fibers, in particular wood pulp fibers which referred to as airfelt, are potentially preferred in certain cases. Examples of absorbent gelling material polymers include polyacrylamides, polyvinyl alcohol, ethylene maleic anhydride copolymers, polyvinyl ethers, hydroxypropyl cellulose, carboxymethyl cellulose, polyvinylmorpholinone, polymers and copolymers of vinyl sulfonic acid, polyacrylates, polyacrylamides, and polyvinyl pyridine. Other types of preferred polymers for use in the absorbent materials are hydrolized, acrylonitrile grafted starch, acrylic acid grafted starch, polyacrylates and isobutylene maleic anhydride copolymers, or mixtures thereof. Even other materials include plastic film of polyethylene, polypropylene, or other flexible moisture impeding material which is substantially water impervious. Any number of these can be used and this is not meant to be an exhaustive list.

Cellophane, mixed with other materials, is yet another example of a potential product that may be implemented within the medication retention layer or other supporting layers. Wax coated cellophane is beneficial over cellophane by itself as plain cellophane is water vapor permeable. Adding wax or other materials such as cellulose nitrate, gum dammar, and paraffin have been used to help prevent permeability. This same concept could potentially be applied to at least part of the composition of a safety layer in addition to the measures described above.

In addition to the medication retention layer being biocompatible, as stated above there could be potentially a neutralizing layer or agent in the overall condom design that would not come into contact with the medication in its routine use (i.e. when the medication does not leak from its intended location). This would be highly variant depending on the type of medication that is to be used. In its preferred form, it would essentially act as an antidote or a neutralizing agent. Very few such remedies exist currently with papaverine having potentially metaraminol as one such example.

Further containment, in conjunction with the previously described measures, could be provided through flexible rings, also called retention bands. In its preferred form, there could be two rings that exist to help contain the medication. For this implement, it differs from similar previous devices as for the purpose of the rings and its additional measures. The first ring separates the first and second sections of the condom as described above. This natural barrier will also help the user to apply the condom in flaccid, semi-erect, and erect states. Previous designs have problems with the condom only being able to be successfully used if the user had an erection. The ring would potentially bypass this problem by allowing the medication to at least initially be placed in a flaccid or semi-erect state until the medication could provide the desired effect leading to the decreased risk of an improperly fitting condom. This ring will also help contain the medication to the first section and further reduce spread to the second section. The second ring in its preferred form exists at the open end of the condom.

Since it contains multiple rings and with a different purpose in mind, these retention bands are different from previous devices. Here, this acts as yet another means to help contain any potential medication leak as described above. It would further potentially help the erection by also acting as an erection ring (also known as a tension ring or cock ring). The rings on the device could be manually adjusted, as well, depending on the choice of the user.

An elastic retention band device can vary in many ways but the desired effect is to provide a firm but comfortable ring around the penis up to the point of restriction of blood flow without the risk of creating a tourniquet. Such devices which create low pressure (such as, as one example, a non-pneumatic tourniquet) may be utilized herein, but without the capability of sliding along the condom article (to prevent forcing blood away from the penis, ostensibly). Rather, the device could be gently yet firmly held in place and have a means to be broken apart for easy removal if needed. At its lower pressure, it is also safer for unintended extended periods of use. It would be adjustable to allow for easier use across a degree of sizes. All of these measures not only assist with containing the medication, but also reduce the risk of bodily fluids from spreading which helps prevent sexual transmitted infections (STIs) and unwanted pregnancy. Additionally, it can contain other measures that may help in this matter such as biocompatible spermicides that would not interact with the other medicaments.

Other materials could be used as it had been in other portions of the condom. In its preferred form, there would exist materials which stretch as demonstrated in the portion for the safety layer. However, it would be designed in such a way as not to counteract the medication. This would include, without limitation, having an absorbable or neutralizing agent. Such iterations would most likely provide some layer as described above which would not risk such complications such as having a normal condom layer.

To further reduce the risk of the condom ripping or otherwise potentially causing a leak of the medication to an unintended part of the condom, a rip-stop design could be implemented. In such an iteration, the material used to keep the condom intact would be interwoven. This design would be unlike anything within the prior condom art. The ideal form would be to reduce the risk of ripping via its interwoven design and should it rip, the condom will only have a small area for which the medication would potentially leak to other layers. This layer could be placed in a number of areas such as a layer between the traditional condom layer and the medication retention layer. Similarly, a mesh design can be used with essentially the same desired effect of reducing such complications and could easily be applied to the traditional condom layer in this invention, as well.

With the multiple means of containment, the medication allows for the user and sexual partner(s) to avoid direct contact of the medication other than to the desired location. This further decreases the risk of unintended absorption or dispersion of the medication. Also, with such containment, this can further attribute to a lower dose of medication needed which in turn helps decrease the risk for adverse events with any medications used. In turn, this allows in the preferred embodiment the option of also still using other routes of medication delivery to assist in its use. In the case for erectile dysfunction, an oral medication can be initially taken at a lower dose. Although this may not allow for a complete erection, it can allow for even easier placement of the male condom compared to applying to a penis that is entirely flaccid. The topical medication is then also applied by its delivery system and allows for the desired erection to become completed. However, this would be done at a lower dose than traditional oral management. Furthermore, as alluded to above, with such an initial oral delivery step and subsequent topical delivery during a single sexual activity, the ED medicament is less likely to stay in the body at levels that are high enough to cause significant complications for the user, including highly unwanted priapism.

In its theorized design, the combination of medicaments both oral and topical improve the delivery within the therapeutic window. By providing an oral medication at a low dose, this can provide assistance for a semi-erect or erect penis at the lower end of the therapeutic window of the medication. In the case of PDE-5 inhibitors, the cGMP pathway is used to create an erection. As nitric oxide (NO) is produced from oxygen and L-arginine under the control of nitric oxide synthase (NOS), the mechanism begins to mediate smooth muscle relaxation to result in an erection. NO stimulated guanylyl cyclase is used to produce cGMP and this lowers intracellular calcium levels. An erection is produced as relaxation of the arterial and trabecular smooth muscle causes arterial dilation and venous constriction. Since PDE-5 is the predominant phosphodiesterase in the corpus cavernosum and degrades cGMP, we want to inhibit this process to promote an erection. By using an oral dose first at a low amount to start the process, we can create a lower threshold for an erection by topical application. The topical medicaments further enhance the therapeutic window and provide a stronger sustaining erection. Given the semipermeable design with a slow and controlled delivery, an erection can obtained until completion of sexual intercourse. Once removed, the small amount of PDE-5 inhibitor that is in the body will decrease through its half-life. By using a lower amount, the erection will return to its flaccid state in a shorter time. This process helps to reduce the risk of complications with prolonged erections or side effects from combinations with other medicaments further supporting the safety of this design.

To facilitate the rapid use of this medication delivery system, warming agents may be used, if so desired. Different external devices, including condom warming devices, including radio-based apparatuses, may be employed. Such warming devices/implements potentially help promote more rapid absorption of the medication allowing for the medication to begin working in a faster manner. Likewise, then, upon removal after ejaculation or the completion of the sexual activity, the lack of further topical delivery allows for quick return to flaccid state to help with the health of the user, at the very least.

Another method of allowing the medication in the condom to work in a potentially faster method is to apply a warming agent topically. A spreadable warming lubricant or a thickened spreadable warming lubricant are examples, including, without limitation lubricants having a mixture of glycerin, polyhydric alcohol, and a non-ionic surfactant (and/or a carbomer thickener). This agent could be applied directly to the skin or to the condom. As with any combination of warming agents, the ideal form is to provide an exothermic reaction.

For that matter, then, exothermic condom packaging may be employed for this purpose as well. While more basic methods of warming can be employed such as menthol, one may also undertake packaging including a plurality of chambers with reactants that then generate a warming effect via and exothermic reaction.

As mentioned above, a number of potential medications could be used. The most common and probably most popular class of medications today is of PDE-5 inhibitors which inhibit phosphodiesterase type 5, enhancing the effects of nitric oxide-activated increases in cyclic guanosine monophosphate (cGMP) which facilitates improved cavernosal smooth muscle relaxation, which results in penile erection. The following are some of the more common medications used currently: sildenafil, tadalafil, vardenafil, avanafil, and zanifil.

Other, non-PDE-5, medications can of course be used. One common medication used is alprostadil which relaxes arterial smooth muscle producing vasodilation and inhibits platelet aggregation (prostaglandin E1). Phentolamine antagonizes alpha adrenergic receptors. Papaverine is an opium alkaloid antispasmodic that has been used in combination with alprostadil alone (or with both medications listed above), in a mixture that is injectable for erectile dysfunction. Aminophylline's exact mechanism of action is unknown but it increases cyclic adenosine monophosphate (cAMP) and antagonizes adenosine receptors (methylxanthine). Isosorbide dinitrate stimulates cGMP production resulting in vascular smooth muscle relaxation. The final non-PDE5 medication that has been used to treat erectile dysfunction to a certain extent is co-dergocrine mesylate but its exact mechanism of action is unknown. Topical vitamins may also be utilized as materials for use with erectile dysfunction situations.

Past utilization of certain ED medicaments, including, for instance, and as non-limiting examples, sildenafil salts, alprostadil and other prostaglandin compositions, have been shown to function in topical forms (even to the extent that possible quicker erection results being obtained with such pure topical applications). Again, the deficiencies of such prior attempts have resided in the manner of such topical usage, particularly as it concerns safety issues for sexual partners and undesirable contact with such medicaments before, during, and after coitus.

There are many ways the medication can be allowed to work. In the preferred embodiment, the medication as a chemical would be contained in such a way as to avoid leakage or early release from the medication retention layer. One possible form consists of a wax bead affixed to the interior surface of the condom which softens in the presence of body heat and exposing the active ingredient. This would be the medication delivery layer. A film layer that erodes during sexual activity due to temperature increase and/or physical contact may also be employed in this capacity. As with medications, a number of combinations could exist but in the preferred embodiment would allow for rapid release from its containing device and promote rapid transdermal absorption to allow for an erection to occur more quickly. Such a delivery layer may thus include alginates, and ethyl vinyl acetate (EVA), as examples, such compound polymers thereof easily wearing away for medicament delivery. Certainly, if desired, the addition of spermicide within the condom interior (whether contacted, covered by a film or wax, for example, therein, as above) can further reduce risk of unwanted pregnancy.

As it concerns initial oral dosing, it is suggested that in the preferred embodiment no more than 50% of the typical oral dose could be used. However, this can be adjusted to values less than or more than 50% should more reasonable amounts be found useful and successful in obtaining the desired results of this design. This could also be based on the individual user's needs where the combination of an oral and topical agent would be 50% of what the oral dose is by itself. For example, if the common prescribed sildenafil citrate (VIAGRA) is dispensed at up to 100 mg daily, the maximum suggested oral dose based on this invention would be 50 mg that is then combined with a topical agent. In another example, if a user typically has a desired effect at 50 mg, they could use 25 mg orally that is then combined with a topical agent. Of course, this can be adjusted as needed along with the topical medication, to create a desired effect. Furthermore, the oral medication could even be repeated if needed to try and use the minimal amount necessary to obtain a state for the penis to allow for better application. For example, if the user usually takes 100 mg daily but wanted to try and use only 25 mg orally, that user could try that and take a second 25 mg oral dose if needed should the first dose not be sufficient after waiting an appropriate amount of time. Again, this emphasizes the use of minimal oral dosing to obtain the effect needed for easier application of the medicated condom. Emphasis is placed to change topical dosing given the potential benefits of decreasing side effects or complications versus oral dosing alone.

Topical dosing would vary widely based on the agent used. Given the number of options as listed above for potential topical agents, and their potential for lower dosing when combined, no definite dosing regimen could be suggested based on the given information currently. However, the preferred embodiment would use the least amount necessary of a medication for the user to have the desired effect.

Essentially, the preferred embodiment would have the following features. The outermost layer as a latex condom with elastic rip-stop or mesh embedded into the walls to help with reinforcing the condom without losing sensitivity or strength. The condom's overall thickness can be between 0.02-0.09 mm in its preferred form. The middle layer would be a double layer membrane which creates a reservoir space that allows it to be semi-permeable. This can contain any number of medicaments and potentially in combination to help treat erectile dysfunction. The inner portion of the double layer will be semi-permeable. To facilitate delivery, the innermost layer could be a material that would break down at room temperature such as a wax bead layer. Once warmed, the medicament in the reservoir is able to be directional toward the penis. In order to best contain, the area where the medication is to be delivered will also have an elastic band that would further contain the medicaments to the desired area which is usually the glans penis. On the proximal end of the condom there would be no medicaments and would consist of the elastic mesh condom layer. This will still help contain should there be any leak. In addition, retention bands will be present to separate the medicated and non-medicated sections as well as at the base of the of the shaft at the open end of the condom, in its preferred embodiment.

In summary, this novel design allows for the safe and effective delivery of a medication used in a male condom while promoting and better utilizing measures to help reduce the risks of UTIs, unwanted pregnancy, and adverse reactions to medications. Although a number of medications can be used, the preferred embodiment is able to decrease the amount of medication needed given its mechanism of delivery to further help reduce the risk of side effects. This can be accomplished in conjunction with other routes of medication, preferably in conjunction with an oral medication.

The inventive condom may be provided commercially within a standard square or other shaped disposable container for removal therefrom by a user. As the ED medicament is stored and sealed within such container (such as, without limitation, a typical tearable plastic square container as typical within the condom industry, again, and removal and placement over and around the user's penis would be well understood. The presence of the medication delivery layer thus prevents (or at least drastically reduces) contact with the actual ED medicament until placed over and around the user's penis. Once sexual congress is completed then, the amount of ED medicament transferred to a body part other than the user's penis would be minimal since diffusion into the penis would be nearly immediate and reliable and any residual amount present on the user's penis would be de minimus although the user may choose to cleanse his hands and penis quickly thereafter to prevent contact with his sexual partner to any appreciable degree.

BRIEF DESCRIPTION OF THE DRAWINGS

FIG. 2 shows a second potentially preferred embodiment of a multi-layer male condom of the invention.

FIG. 3 shows a flow chart of the method of use of said male condom for controlled erection generation and reduction during a sexual activity.

DETAILED DESCRIPTION OF THE PREFERRED EMBODIMENTS AND DRAWINGS

Figure 1:
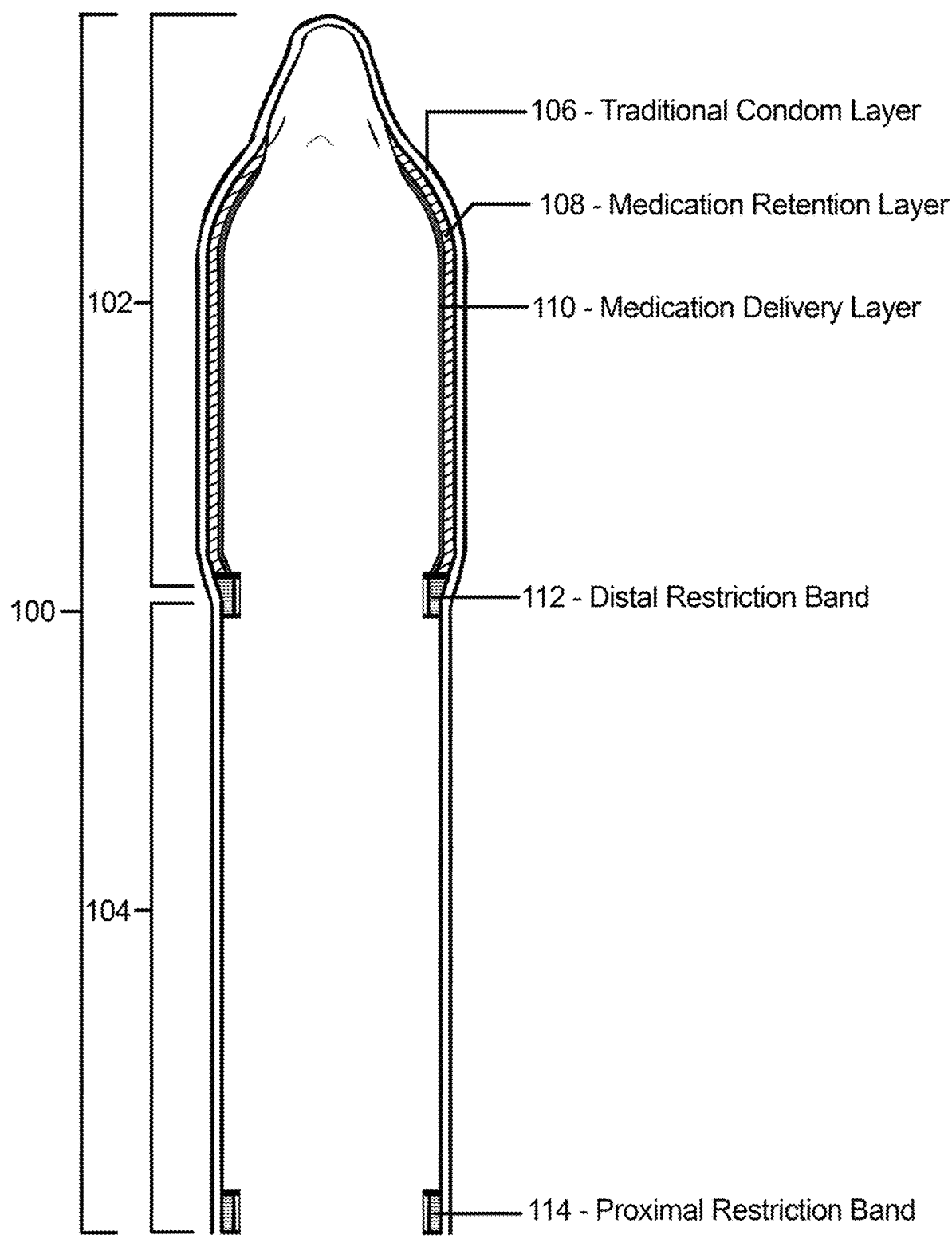
FIG. 1 shows a cross-section view of a potentially preferred embodiment of a multi-layer male condom including ED medicaments therein.

Without any intention of limiting the scope of the inventive device/method, the drawings described herein provide but certain possible embodiments herein. Various modifications and different configurations of such a device/method may be employed without deviating from the scope and basis of the present invention.

FIG. 1 thus shows one preferred embodiment medicament delivery condom 100 having a distal region 102 and a proximal region 104. The distal region 102 thus includes the above described traditional condom layer 106 (made from standard condom latex, as one example, and having a thickness of from 0.05 to 2 mils, more preferably from about 1 to 1.5 mils), medication retention layer 108 (including the medicament and having a thickness of from 0.05 to 2 mils, itself, preferably from 0.08 to 0.8 mils), medication delivery layer 110 (as described above, and also having a thickness of from 0.05 to 2 mils, preferably from 0.08 to 0.8 mils), and distal retention band 112. The thinner, yet sufficiently strong outer layer 106, coupled with the other interior layers 108, 110, provide greater sensitivity for the user. The distal retention band 112 functions to reduce the chance (if not prevent) migration of a medicament from this distal region 102 of the condom 100, ostensibly, as noted above, to reduce the chance of contact with a sexual partner during coitus and afterwards. Such a distal retention band 112 is provided with a low-pressure application to the user's penis (within the distal region 112), but such may function to provide some degree of stimulation to the user even with a low-pressure application. For this embodiment, such a distal region band 112 (and the proximal region band 114, for that matter) is provided as an internal component contacting and attached to the inner lining of the traditional outer condom layer 106 for greater reliability for such a purpose as noted above. In this potentially preferred embodiment, the traditional condom layer 106 may consist of a mesh or rip-stop design and potentially other methods as described above to help prevent any ripping, tearing, or other types of breakage to the outer layer 106 of the condom or may be provided as a standard latex component as well. The medication retention layer 108 remains as the layer to contain the medicaments to be delivered, including a wax, bead, or other type of erodible base that, for instance, wears away gradually upon exposure to the user's own elevated body temperature, thereby allowing for migration of the medicament inwards towards the glans penis of the user, for instance. Innermost, and directly against the skin of the glans penis, is the medication delivery layer 110 that allows for migration from the medication retention layer 108 thereto for contact topically with a user's penis within the distal region 102 of the condom 100. In conjunction with the medication retention layer 108, this allows for the controlled delivery of the medicaments to the desired locations of the user's penis for effective diffusion within the skin to capillaries (blood vessel beds) therein to generate nitric oxide, etc., as needed for erection generation. There is a second retention band 114 at the proximal (open) end of the condom 100 for effective pressure-generated contact to the base of the user's penis to not only keep the condom 100 in proper place before, during, and after sexual congress, but also to act as a second line of defense to reduce the chance (if not prevent) medicament migration outside the condom 100, itself, for protection of the user's sexual partner. Thus, the medication retention layer 108 gradually wears away and provides a very thin layer that does not appreciably affect the overall sensitivity properties of the condom 100 in relation to the user (ostensibly, combined with the thin medication delivery layer 110, neither layer 108, 110 prevents the pleasurable aspects of such a sexual event for the user.

FIG. 2 shows a second potential preferred embodiment condom 200. This embodiment includes a distal region 202 and a proximal region 204, with two traditional condom layers 206 (of, as merely an example, standard condom latex material, and thicknesses of from 0.05 to 1.5 mils each, more preferably from 0.075 to 1 mils each), 210 sandwiching an additional safety layer 208 in between (of from 0.025 to 0.1 mils thickness). Such an extra safety layer 208 provides greater strength, for instance, to prevent tearing, ripping, etc., of the overall condom 200 during coitus. The safety layer 208 thus may also contain a number of measures to help avoid an external leak of the medication from the medication retention layer 210 in an outward fashion. As described above, this can contain but is not limited to such measures as a neutralizing agent, products that can stretch to a significant amount where it would not break such as those that are gelatin-based, materials designed to absorb the medicaments, and even other measures such as cellophane potentially mixed with other materials. Although in this example the inner traditional condom layer 210 and the additional safety layer 208 are only at the area of the distal section of the condom 202, these could extend the entire length of the condom if desired. Also, different in this design is the retention band placement as both the distal band 216 and proximal band 218 are provided externally to the traditional condom layer 206. In this example, the retention bands 216, 218 are on the exterior portion of the condom versus the first potential preferred embodiment where it was interior. This is to show that the retention bands can be placed internally, externally, or even in combination, if desired. Such placement would vary depending on the materials used and their purpose (as well as the choice of the user). As for the FIG. 1 condom 100, the medication retention layer 212 is present to wear away upon exposure to heat and friction and the medication delivery layer 214 allows for controlled migration of the released ED medicament for diffusion to the user's penis. This ability to control such delivery thus allows for continued generation of nitric oxide, etc., as needed for erection provisions for the user. Upon removal of such a condom (100 or 200), the user does not have any further exposure to such an ED medicament and thus the generation of needed compounds (nitric oxide, etc.) stops and the user returns to flaccid state (to prevent priapism, at least).

FIG. 3 depicts a flow chart 300 of the method of use of said male condom. It covers the method for controlled erection generation and reduction during a sexual activity. First, the user would take the oral medication 302 as described above. When the user has reached a desired state of erection 304 for easier placement of the condom, this can then be applied to the user 306. This would not need to be a full erection, can be applied in a flaccid or semi-erect state. After application of the condom and desired erection is obtained by the user 308, a sexual event may occur until completed or as desired by the user 310. Upon completion, the user's condom is removed from the penis 312 to allow the medication to stop being delivered topically 314. With time, the user's penis will return to a flaccid state 316. As the ED medicament quickly and effectively diffuses within the user's skin on contact, any residual amounts will most likely be minimal at best and probably will not be present at all. Of course, in order to best ensure contact of such a medicament with the user's partner may involve immediate cleansing of the user's penis thereafter such an activity to even further ensure such a partner will not contact or have any appreciable direct exposure to the medicament itself.

Thus, a condom implement with all-in-one ED medicament topical application means before and during a sexual event is provided for controlled ED medicament delivery and immediate cessation thereof when sexual congress is completed to allow for flaccid state to return quickly. Additionally, the configuration of the condom 100, 200 itself provides an effective manner of preventing any appreciable potential contact of the user's sexual partner with an ED medicament before, during, and after coitus. For that matter, with the medication delivery layer 110, 214 providing any contact with the user upon removal, for instance, of the condom 100, 200 from a storage package for placement over the user's penis, and the lack of sufficient heat and/or friction at that moment in time to cause the erosion, etc., of the medication retention layer 108, 212 until such penis placement, again, the chances of partner contact with such an ED medicament is extremely low, if at all. As such, the inventive condom 100, 200 and method of use 300 provides an effective STD avoidance platform coupled with a means to deliver topically an ED medicament for a male experiencing ED issues, where the sexual partner does not have any appreciable exposure to such a topically applied ED medicament. Furthermore, the topical delivery component of the method may be coupled with an oral delivery initial step simply to generate an initial erection status for effective placement and retention of the condom 100, 200 around and over the subject user's penis during sexual congress with a partner. Upon removal of such a topical delivery condom 100, 200, the effect is nearly immediate that the user will experience erection loss since the continuous stream of ED medicament ends and the initial oral delivery step simply exists to provide n initial erection for more effective placement over and around the user's penis. Such an overall implement and method thus accords a means to this degree that has not been disclosed in the prior art of this industry.

Having described the invention in detail it is obvious that one skilled in the art will be able to make variations and modifications thereto without departing from the scope of the present invention. Accordingly, the scope of the present invention should be determined only by the claims appended hereto.

What I claim is:

1. A male condom sheath having a closed distal region defined as covering a user's glans penis when situated over and around such a user's penis, and an open proximal region defined as the remainder of said condom having a top edge abutting said bottom edge of said distal region and a bottom edge at the opening of said condom, said condom comprising at least three layers of flexible material within the sheath thereof within said closed distal region, wherein one of said at least three layers is an outer layer for contact with a sexual partner when in use, wherein one of said at least three layers is a material for retention of erectile dysfunction medicament therein for migration therefrom when exposed to heat and friction during a sexual activity, and wherein one of said at least three layers is an inner layer material for erectile dysfunction medicament delivery to the surface of said user's skin; wherein said open proximal region does not comprise said material for retention of erectile dysfunction medicament but does include the same flexible material as said outer layer for contact with a sexual partner when in use; wherein said condom further includes a flexible, pressure ring at the bottom edge of said distal region and a second flexible, pressure ring at the bottom edge of said proximal region.

2. A method of utilizing such a male condom as described in claim 1, the method comprising:
  i) providing said male condom to a user,
  ii) providing an oral erectile dysfunction medicament to the same user, wherein said oral medicament includes a dosage level of at most 50% of the typical oral dose, a level that allows for the generation of an initial erection for said user to the extent that said male condom may then be placed over and around said initial erection,
  iii) the undertaking of sexual activity by said male user with said male condom remaining in place until ejaculation has been attained or such sexual activity ceases, and
  iv) subsequent removal thereof of said male condom from said user's erection, thereby resulting in the lack of further topical medicament in contact with said user's penis thus allowing for return of said penis to flaccid state.

* * * * *